(12) United States Patent
Zhong et al.

(10) Patent No.: US 12,054,452 B2
(45) Date of Patent: Aug. 6, 2024

(54) METHOD AND SYSTEM FOR PREPARING XANTHATE BY SLURRY METHOD

(71) Applicant: CENTRAL SOUTH UNIVERSITY, Hunan (CN)

(72) Inventors: Hong Zhong, Hunan (CN); Xin Ma, Hunan (CN); Shuai Wang, Hunan (CN)

(73) Assignee: CENTRAL SOUTH UNIVERSITY, Hunan (CN)

( * ) Notice: Subject to any disclaimer, the term of this patent is extended or adjusted under 35 U.S.C. 154(b) by 947 days.

(21) Appl. No.: 17/005,324

(22) Filed: Aug. 28, 2020

(65) Prior Publication Data

US 2020/0392080 A1 Dec. 17, 2020

Related U.S. Application Data

(63) Continuation of application No. PCT/CN2018/119611, filed on Dec. 6, 2018.

(30) Foreign Application Priority Data

Aug. 7, 2018 (CN) .......................... 201810890358.4

(51) Int. Cl.
*C07C 329/16* (2006.01)
*B03D 1/002* (2006.01)
*B03D 1/14* (2006.01)

(52) U.S. Cl.
CPC ............ *C07C 329/16* (2013.01); *B03D 1/002* (2013.01); *B03D 1/14* (2013.01); *B03D 2201/007* (2013.01); *B03D 2201/02* (2013.01); *B03D 2203/02* (2013.01)

(58) Field of Classification Search
CPC ..................................................... C07C 329/16
See application file for complete search history.

(56) References Cited

U.S. PATENT DOCUMENTS 5,239,104 A * 8/1993 Shaw .................... C07C 329/16
558/247

* cited by examiner

*Primary Examiner* — Shawquia Jackson

(57) ABSTRACT

A method for preparing xanthate by a slurry method includes steps of: adding a mixture of dichloromethane and carbon disulfide as a reaction solvent in a slurry reactor, and then adding alcohol and caustic alkali to react with carbon disulfide under less than 1 atm to remove heat released by the reaction by evaporating the solvent; performing vacuum distillation after the reaction to remove the solvent and water, so as to obtain the xanthate; transporting the xanthate to a granulation equipment for granulating, and then drying in a drying equipment to obtain a product. The method is performed in a system formed by a reaction equipment, a solvent recovery equipment, the granulation equipment, and the drying equipment, wherein a main equipment of the reaction system is a slurry reactor. The method has advantages of high efficiency, low energy consumption, good safety, environmental friendliness, convenient operation and the like.

6 Claims, 2 Drawing Sheets

METHOD AND SYSTEM FOR PREPARING XANTHATE BY SLURRY METHOD

CROSS REFERENCE OF RELATED APPLICATION

The application is a continuation application of a PCT application No. PCT/CN2018/119611, filed on Dec. 6, 2018; and claims the priority of Chinese Patent Application No. CN201810890358.4, filed to the State Intellectual Property Office of China (SIPO) on Aug. 7, 2018, the entire content of which are incorporated hereby by reference.

BACKGROUND OF THE PRESENT INVENTION

Field of Invention

The present invention relates to a technical field of preparation methods of chemical mineral processing reagents, and more particularly to a method and a system for preparing xanthate by a slurry method.

Description of Related Arts

Xanthate, also known as xanthogenate or dithiocarbonate, has a structural formula of:

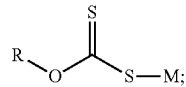

wherein R is a hydrocarbon group of different carbon chains and M is usually Na or K. Xanthate was first synthesized by Zeise in 1815. Not until 1925, when Keller discovered that xanthate could be used as a flotation collector for non-ferrous metal sulfide ores, was xanthate widely used in metal sulfide mines and metal sulfide mineral recovery, which then greatly promoted the development of the mineral flotation industry. Conventionally, xanthate is still the most universal and important sulfide ore collector.

Conventionally, the industrial production of xanthate mainly uses the kneading method. According to this method, alcohol and carbon disulfide are added to the kneader, and then powdered caustic alkali is added in batches to knead and synthesize the xanthate. The production of xanthate by the kneading method suffers from the following problems: the particle size of the alkali is required to be fine, and the energy consumption for powdering the alkali is high; the reaction of synthesizing xanthate is highly exothermic, and needs a high-power refrigerator to strictly control the reaction temperature, otherwise it will not only seriously affect the quality of the product, but may also cause danger; it is difficult to achieve closed production by the kneading method, wherein there is a small amount of volatile losses such as carbon disulfide in the production process; furthermore, the temperature is not easy to control during the production process, resulting in incomplete reactions, more side reactions, and low purity. The xanthate product produced by the kneading method contains water and has a high content of impurities, especially unreacted caustic alkali, resulting in a short shelf life of the product (see Tian Xishuang, Wang Yongxin. Discussion on the production method of xanthate. Nonferrous Metals (Mineral Processing Section) 1991(03): 30-31; and Xiong Xin. Production practice of xanthate synthesis process. Copper Engineering, 2003(2): 29-31). It is also reported in the literature that wet alkali method is used to prepare the xanthate. According to such method, a small amount of water is added during the production of sodium alkoxide to moisten the caustic soda, thereby avoiding agglomeration of the caustic soda and completing the reaction. The prepared sodium alkoxide then reacts with carbon disulfide to form xanthate (that is, a xanthate aqueous solution). Liquid xanthate products have the advantages of low production cost, no need to dissolve when used, easy operation, and controllable amount of free alkali in the product. This method is mainly suitable for small-scale location production. However, the liquid xanthate is unstable and difficult to store, which greatly limits its application (Yang Xiaoling, Zhang Hongliang. Synthesis of liquid isopropyl xanthate. Applied Chemical Industry, 2010, 39(6): 895-897).

It is reported in the literature that the solvent method is used to synthesize xanthate. The xanthate product synthesized by the solvent method has the advantages of high purity and yield, but usually requires a large amount of solvent, complicated operation, high energy consumption, and relatively high production cost (see Shi Xianyi, Qin Xuemei, Deng Zhongyan. Improvement of synthetic technology of butyl sodium xanthate[J]. Chemical Technology and Development, 2006, 35(4): 47-48; Hu Zhengji, Wang Shiyue, Wang Qingjiu, Qu Zhiqiang. Solvent method production of isobutyl potassium xanthate [J]. Nonferrous Mining and Metallurgy, 1999 (4): 16-18; Konrad Baessler, Georg Polz. Process for the manufacture of alkali xanthates [P]. AU1713170A, 1970-7-3; Tian Xishuang, Wang Yongxin. Discussion on the production method of xanthate [J]. Nonferrous Metals (Mineral Processing Section) 1991 (03): 30-31; A. M. Ahmed, K. Ibrahim, O. R. Anna, P. F. Jr John. Synthesis, characterization and luminescent properties of dinuclear Gold(I) xanthate complexes: X-ray structure of [Au$_2$(n-Buxanthate)$_2$][J]. Inorg Chem 2004, 43:3833-3839; Huang Jun. A synthetic technology of butyl sodium xanthate [P]. CN102050769A, 2011-05-11; Ma Xin, Zhong Hong, Wang Shuai, Hu Yuan, Xiao Jingjing. Solvent synthesis of sodium isobutyl xanthate[J]. Journal of Jiangxi University of Science and Technology, 2012, 3(5): 1-5; Zhong Hong, Liu Guangyi, Ma Xin, Wang Shuai, Cao Zhanfang. A synthetic method of xanthate[P]. CN102690218A, 2012-09-26; Xin Ma, Shuai Wang, Hong Zhong. Effective production of sodium isobutyl xanthate using carbon disulfide as a solvent: reaction kinetics, calorimetry and scale-up[J]. Journal of Cleaner Production, 2018, 200: 444453; and Liu Guangyi, Huang Yaoguo. Preparation of xanthate[P]. CN 105384669 A. 2016-03-09).

The conventional solvent method for preparing xanthate is to react caustic alkali, carbon disulfide and alcohol in an organic solvent medium to prepare xanthate. After the reaction, slurry obtained by the reaction is transferred to a drying device (such as a rake dryer) to remove the solvent and obtain the xanthate. During synthesizing xanthate by the reaction of alcohol, carbon disulfide and caustic alkali, the reaction itself is an exothermic process, the reaction rate is fast, and the reaction exothermic heat is large. Although the organic solvent slows down the severity of the reaction and avoids aggravating side reactions due to excessive local temperature, a large amount of cooling water is still needed to remove the heat released by the reaction and to control the reaction temperature. After the reaction, it needs to be heated to a certain temperature to remove the solvent by distillation. The entire process is complicated, with low energy utilization and high energy consumption.

SUMMARY OF THE PRESENT INVENTION

In view of the above technical problems in the prior art, the present invention provides a method and a system for preparing xanthate by a slurry method. The method can not only reduce volatilization loss of carbon disulfide, but also control a temperature during a preparation process. As a result, product purity is high; the prepared xanthate is stable and easy to store; little solvent is required in the production process and operation is simple; and less cooling water is used in reaction process and the energy consumption is low.

Accordingly, in order to accomplish the above object, the present invention provides:

a method for preparing xanthate by a slurry method, comprising steps of:

1) adding dichloromethane and carbon disulfide into a slurry reactor and mixing through stirring, then adding alcohol and alkali and stirring for reaction;

2) turning on a vacuum pump to adjust a system pressure when a temperature of a reaction system begins to rise, so as to control the temperature of the reaction system and recover a solvent; and 3) injecting hot water or steam into a heating jacket of the slurry reactor after the solvent is recovered, so as to accelerate removal of the solvent and obtain powdered xanthate.

Preferably, the method further comprises a step of: transferring the powdered xanthate to a granulation equipment for granulation: drying and dehydrating granules obtained by granulation to obtain granular xanthate.

Preferably, in the step 1), 2-tert-butoxyethanol is also added.

Preferably, an addition amount of 2-tert-butoxyethanol is 5%-10% by weight of the alcohol. The addition of the 2-tert-butoxyethanol enables the powder product to have a certain viscosity, which is conducive to subsequent granulation.

Preferably, a molar ratio of the alcohol, the alkali and the carbon disulfide is 1:1-1.05:1-3, and a volume of the dichloromethane is 0.5-5 times a volume of the alcohol.

Preferably, in the step 2), the system pressure is controlled at −0.01--0.08 MPa; and the temperature of the reaction system is maintained at 10-80° C.

Preferably, the alcohol is $C_2$-$C_{12}$ fatty alcohol, fusel oil, $C_2$-$C_{10}$ alkoxy ether alcohol or a combination thereof.

Preferably, the $C_2$-$C_{12}$ fatty alcohol is selected from the group consisting of ethanol, n-propanol, isopropanol, n-butanol, isobutanol, amyl alcohol, isoamyl alcohol, neopentyl alcohol, n-hexanol, isohexanol, methyl isobutyl carbinol, n-octanol, isooctyl alcohol, and dodecanol.

Preferably, the $C_2$-$C_{10}$ alkoxy ether alcohol is selected from the group consisting of 2-methoxyethanol, 2-propoxyethanol, 2-butoxyehanol, 2-tert-butoxyethanol, 2-hexyloxyethanol, 2-methoxypropanol, 2-ethoxypropanol and 2-butoxypropanol.

Preferably, the reaction lasts for 0.5-6h.

Preferably, the alkali is caustic, such as sodium hydroxide or potassium hydroxide, in shape of powder, granule or flake.

According to the present invention, a reaction temperature for synthesizing the xanthate is 0-70° C., and a reaction time is 0.5-6h. A temperature in the reactor can be adjusted by changing a solvent distillation pressure or control a solvent evaporation rate.

The present also provides a system of the method for preparing the xanthate by the slurry method, comprising: a reaction device, a solvent recovery device, a granulation equipment and a drying equipment, which all communicate with each other; wherein the reaction device comprises a slurry reactor, a raw material inlet, a powder outlet, a gas outlet, and a stirrer; wherein the raw material inlet, the powder outlet, and the gas outlet are provided on the slurry reactor; and the stirrer is installed in the slurry reactor:

the solvent recovery device comprises a dust collector, a condenser, a vacuum pump, and a plurality of activated carbon adsorption columns, which are all sequentially connected; wherein the dust collector is connected to the gas outlet:

the condenser and the activated carbon adsorption columns are both connected to a solvent storage tank; and the activated carbon adsorption columns are connected to each other through pipes;

the granulation equipment comprises a granulation equipment body, a powder inlet, and a granule outlet; wherein the powder inlet and the granule outlet are located at two ends of the granulation equipment body, respectively; and the powder inlet is connected to the powder outlet;

the drying equipment comprises a drying equipment body, a drying jacket, a granule inlet, an exhaust outlet, and a product outlet; wherein the exhaust outlet is connected to the dust collector.

Preferably, the stirrer is a spiral ribbon stirrer or a spiral stirrer.

Preferably, the raw material inlet comprises an alkali inlet, an alcohol inlet, a dichloromethane inlet, and a carbon disulfide inlet: wherein the alkali inlet is connected to an alkali storage tank; the alcohol inlet is connected to an alcohol storage tank; the dichloromethane inlet is connected to a dichloromethane storage tank; and the carbon disulfide inlet is connected to a carbon disulfide storage tank.

Preferably, a heating jacket, connected to a heating equipment, is provided on a sleeve of the slurry reactor.

Preferably, the activated carbon adsorption columns directly communicate with a gas release valve communicating with atmosphere, or directly communicate with the vacuum pump through a gas intake valve. Heads of the activated carbon adsorption columns communicate with each other through pipes, so do the tails of the activated carbon adsorption columns, wherein communications can be switched in parallel or in series through valves. Preferably, there are three activated carbon adsorption columns, wherein two out of three are connected in series for adsorption by adjusting the valves, and the other is used in parallel with the former two for desorption or standby. Preferably, the activated carbon adsorption columns comprise an activated carbon adsorption column I, an activated carbon adsorption column II, and an activated carbon adsorption column III, wherein two of the activated carbon adsorption columns cooperate in series to adsorb the solvent and discharge to the atmosphere; the other is connected in parallel for standby or desorption.

Preferably, the granulation equipment is a screw extruder or double-roller rounder. More preferably, the screw extruder is a single-screw extruder or a twin-screw extruder. More preferably, the granulation equipment is the twin-screw extruder.

Preferably, the drying jacket comprises a drying jacket body, a steam inlet pipe, and a condensed water outlet: wherein the steam inlet pipe and the condensed water outlet are located on two sides of the drying jacket body, respectively.

Preferably, the drying equipment is a multi-layer disc dryer, a rotary cylinder dryer or a belt dryer. More preferably, the drying equipment is a multi-layer disc dryer.

Preferably, the solvent storage tank comprises a water valve and a solvent valve.

According to the method of the present invention, reaction, solvent removal, and drying and dehydration are completed in a main reaction device of the system—the slurry reactor. The method is simple in operation and has characteristics of high mixing speed, high efficiency, and fast discharge, which can meet requirements of vacuum feeding and dust free.

According to the method of the present invention, the solvent in the slurry reactor is evaporated by the vacuum pump during reaction, thereby taking away most of the heat released by preparing the xanthate, which requires less cooling water during the reaction, reduces the reaction temperature, accelerates a feeding speed, and shortens production cycle. The vacuum pump can maintain the reaction under 1 atm, so as to recover the solvent while reducing the heat of reaction. The solvent evaporation rate can be adjusted by adjusting a pressure of the vacuum pump, thereby controlling the temperature of the reaction system.

In the method of the present invention, all removed solvent enters a solvent recovery system in which the solvent is directly recovered after dust removal and condensation, wherein gas is processed with adsorption before discharging without pollution. The recovered solvent enters the solvent storage tank, wherein the liquid water is separated and floats above the solvent, which forms a water seal. The water can be discharged through a water discharge valve after accumulating to a certain.

The xanthate product prepared by the present invention has high purity and yield, less impurities, while the preparation process is easy to operate, low in cost, environmentally friendly, and easy to realize industrial production.

BENEFICIAL EFFECTS OF THE PRESENT INVENTION

The method and the system of the present invention for preparing the xanthate by the slurry method have specific advantages as follows.

(1) When using the method of the present invention to prepare the xanthate, the reaction system is in a slurry form, wherein the system is uniform, mass and heat transfer of the reaction system are relatively uniform, and contact of reactants is sufficient to facilitate the reaction.

(2) According to the present invention, a mixture of the dichloromethane and the carbon disulfide is used as the reaction solvent, and the reaction is performed under less than 1 atm. The heat of reaction is removed by vaporization of the solvent, so as to control the reaction temperature. Since the solvent vaporization can take away the heat of reaction more efficiently, an amount of the solvent needed can be significantly reduced. A minimum amount of the solvent is only 1.0 times a volume of the raw material alcohol, which reduces energy consumption required for solvent evaporation and no more requires a large amount of solvent as a solvent method do.

(3) A boiling point of the dichloromethane is 39.8° C., and that of the carbon disulfide is 46.5° C. The boiling points are low, and the one of dichloromethane is even lower than that of the carbon disulfide. The low boiling point facilitates volatilizing and heat removing, which is conductive to recycling of solvent. Furthermore, dichloromethane has a flame-retardant effect. A closed flash point of the reactant carbon disulfide is −30° C., which will be significantly improved when dichloromethane is added (as shown in FIG. 2). For example, when a volume fraction of dichloromethane is 500%, the closed flash point is increased to 31.2±1° C., which shows that dichloromethane, as the reaction solvent, can effectively improve the safety of the process.

(4) In preparation of the present invention, the slurry reactor integrates functions of reaction, solvent removal, as well as drying and dehydration. The method is simple in operation, and the slurry reactor has characteristics of high mixing speed, high efficiency, and fast discharge, which can meet requirements of vacuum feeding and dust free.

(5) The system of the present invention integrates reaction equipment, solvent recovery equipment, granulation equipment, drying equipment, and material drying equipment. Connections of each component is simple and effective, which are conductive to automatic control of production lines. Energy utilization efficiency is high and energy consumption is low.

(6) According to the present invention, raw material conversion rate, product yield and purity are high, while energy consumption is low. The entire production process is operated in a closed system, which is free of exhaust gas emission, eco-friendly, and easy to realize industrialization.

BRIEF DESCRIPTION OF THE DRAWINGS

In order to explain embodiments of the present invention or technical solutions in the prior art more clearly, drawings involved in the embodiments will be briefly introduced below. Obviously, the drawings in the following description are only some embodiments of the present invention. For those of ordinary skill in the art, without paying any creative work, other drawings may be obtained based on these drawings.

Figure 2:
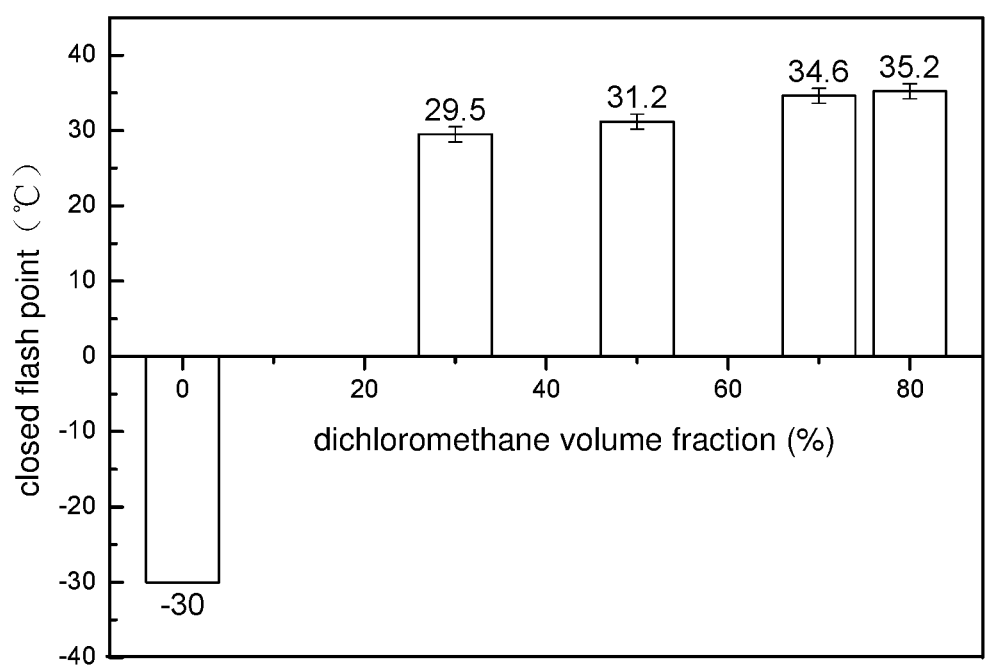

Element Reference:

1—reaction device: 1-1—slurry reactor, 1-2—alkali storage tank; 1-3—alcohol storage tank; 1-4—dichloromethane storage tank; 1-5—carbon disulfide storage tank; 1-6—powder outlet:

2—solvent recovery device: 2-1—dust collector; 2-2—condenser; 2-3—vacuum pump; 2-4—activated carbon adsorption column I: 2-5—activated carbon adsorption column II; 2-6—activated carbon adsorption column III: 2-7—solvent storage tank:

3—granulation equipment: 3-1—powder inlet: 3-2—granule outlet;

4—drying equipment: 4-1—granule inlet; 4-2—exhaust outlet; 4-3—steam inlet pipe; 4-4—product outlet; 4-5—condensed water outlet;

FIG. 2 illustrates test results of a closed flash point of a mixed solution of dichloromethane and carbon disulfide.

DETAILED DESCRIPTION OF THE PREFERRED EMBODIMENT

Technical solutions in embodiments of the present invention will be described clearly and completely with the accompanying drawings. Obviously, the described embodiments are only a part of all the embodiments of the present invention. Based on the described embodiments, all other embodiments obtained by those of ordinary skill in the art fall within the protection scope of the present invention.

Unless otherwise defined, all technical terms used below have the same meaning as commonly understood by those skilled in the art. The technical terms herein are used for describing specific embodiments only, and not intended to be limiting.

Unless otherwise specified, various reagents and raw materials used in the present invention are commercially available products or products that can be prepared by known methods.

Embodiment 1

Figure 1:
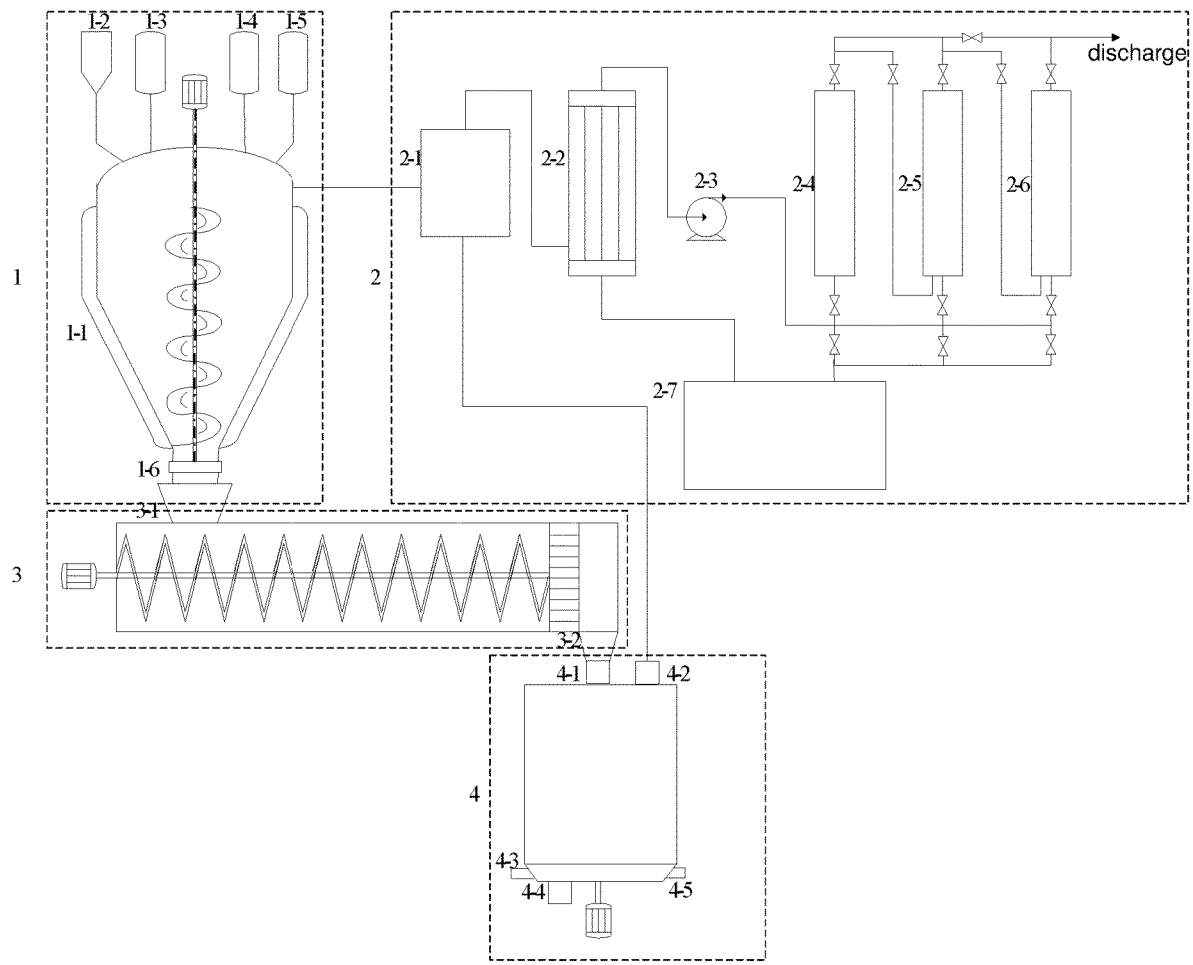
FIG. 1 is a system structural view of an embodiment of the present invention.

Referring to FIG. 1, the present provides a system of a method for preparing xanthate by a slurry method, comprising: a reaction device 1, a solvent recovery device 2, a granulation equipment 3 and a drying equipment 4, which all communicate with each other.

The reaction device 1 comprises a slurry reactor 1-1, a raw material inlet, a powder outlet 1-6, a gas outlet, and a stirrer; wherein the raw material inlet, the powder outlet 1-6, and the gas outlet are provided on the slurry reactor 1-1; and the stirrer is installed in the slurry reactor 1-1. Preferably, the stirrer is a spiral ribbon stirrer or a spiral stirrer. The spiral ribbon stirrer is a single-ribbon stirrer or a double-ribbon stirrer, more preferably the double-ribbon stirrer, which is conducive to stirring a sludge product of the slurry method and subsequent solvent removal. Preferably, the raw material inlet comprises an alkali inlet, an alcohol inlet, a dichloromethane inlet, and a carbon disulfide inlet: wherein the alkali inlet is connected to an alkali storage tank 1-2; the alcohol inlet is connected to an alcohol storage tank 1-3; the dichloromethane inlet is connected to a dichloromethane storage tank 1-4; and the carbon disulfide inlet is connected to a carbon disulfide storage tank 1-5. Preferably, a heating jacket, connected to a heating equipment, is provided on a sleeve of the slurry reactor 1-1. The heating jacket is conducive to subsequent removal of residual water or the solvent in the slurry reactor 1-1. Preferably, the slurry reactor 1-1 comprises a temperature detector and a pressure detector, wherein both are connected to a controller, and the controller is connected to a vacuum pump 2-3. Reaction temperature and pressure in the slurry reactor 1-1 are detected through the temperature detector and the pressure detector, so as to control working parameters of the vacuum pump 2-3.

The solvent recovery device 2 comprises a dust collector 2-1, a condenser 2-2, a vacuum pump 2-3, and a plurality of activated carbon adsorption columns, which are all sequentially connected.

The dust collector 2-1 is connected to the gas outlet. The solvent in the slurry reactor 1-1 enters the dust collector 2-1 in a gas form with dust, and passes through the dust collector 2-1 for removing the dust before entering subsequent devices.

The condenser 2-2 and the activated carbon adsorption columns are both connected to a solvent storage tank 2-7.

The activated carbon adsorption columns are connected to each other through pipes. Heads of the activated carbon adsorption columns communicate with each other through pipes, so do the tails of the activated carbon adsorption columns, wherein communications can be switched in parallel or in series through valves. Preferably, there are three activated carbon adsorption columns, wherein two out of three are connected in series for adsorption by adjusting the valves, and the other is used in parallel with the former two for desorption or standby. The activated carbon adsorption columns directly communicate with a gas release valve communicating with atmosphere, or directly communicate with the vacuum pump 2-3 through a gas intake valve.

According to the embodiment 1, the activated carbon adsorption columns comprise an activated carbon adsorption column I 2-4, an activated carbon adsorption column II 2-5, and an activated carbon adsorption column III 2-6, wherein two of the activated carbon adsorption columns cooperate in series to adsorb the solvent and discharge to the atmosphere; the other is connected in parallel for standby or desorption.

The granulation equipment 3 comprises a granulation equipment body, a powder inlet 3-1, and a granule outlet 3-2.

The powder inlet 3-1 and the granule outlet 3-2 are located at two ends of the granulation equipment body, respectively. Preferably, the granulation equipment 3 is a screw extruder or double-roller rounder, wherein the screw extruder is a single-screw extruder or a twin-screw extruder. More preferably, the granulation equipment 3 is the twin-screw extruder. The powdered xanthate is made into granular xanthate, which is beneficial to subsequent products.

The powder inlet 3-1 is connected to the powder outlet 1-6.

The drying equipment 4 comprises a drying equipment body, a drying jacket, a granule inlet 4-1, an exhaust outlet 4-2, and a product outlet 4-4. Preferably, the drying jacket comprises a drying jacket body, a steam inlet pipe 4-3, and a condensed water outlet 4-5; wherein the steam inlet pipe 4-3 and the condensed water outlet 4-5 are located on two sides of the drying jacket body, respectively. The exhaust outlet 4-2 is connected to the dust collector 2-1 to discharge without pollution. Preferably, the drying equipment 4 is a multi-layer disc dryer, a rotary cylinder dryer or a belt dryer. More preferably, the drying equipment 4 is a multi-layer disc dryer.

Embodiment 2: Preparing Sodium Isobutyl Xanthate with the System of the Embodiment 1

Adding 34.0 parts of 99% pure dichloromethane and 18.3 parts of 99% pure carbon disulfide to a slurry reactor, turning on a reactor stirring device, and then adding 6.4 parts of granular sodium hydroxide (99% pure) to the reactor; then dropping 11.8 parts of 99% pure isobutanol into the reactor; when material temperature in the reactor rises rapidly with reaction, turning on a vacuum pump and a condenser in a solvent recovery system to control an evaporation rate of a solvent in the reactor by adjusting a vacuum degree; then maintaining a reaction temperature in the reactor at 25-30° C., and reacting for 2.5h; wherein at this time, the material in the reactor is a sludge form.

Injecting 50-80° C. hot water into a jacket of the reactor, and drying for 1h under a vacuum degree of −0.04--0.05 MPa, so as to obtain powdered sodium isobutyl xanthate as well as recover the solvent.

Opening a discharge valve of the reactor to transfer the powdered sodium xanthate obtained by the reaction into a twin-screw extruder for granulation, so as to obtain granular sodium xanthate with a size of about Φ4×6-12 (mm).

Sending the granular sodium xanthate into a disc dryer for further drying to remove residual solvent and a part of water at a drying temperature of 50-120° C., so as to obtain a dried granular sodium isobutyl xanthate product as well as recover the solvent.

Analysis showed that the sodium isobutyl xanthate product had a purity of 91.16%, a free base content of 0.11%, and a moisture content of 2.92%. A yield of the product based on isobutanol was 95.68%, and the product reached a standard dry product of nonferrous metal industry.

Embodiment 3: Preparing Sodium Isobutyl Xanthate with the System of the Embodiment 1

Adding 34.0 parts of 99% pure dichloromethane, 18.3 parts of 99% pure carbon disulfide, and 11.8 parts of 99% pure isobutanol to a slurry reactor, turning on a reactor stirring device, and then adding 6.4 parts of flake sodium hydroxide (99% pure) to the reactor in batches; when material temperature in the reactor rises rapidly with reaction, turning on a vacuum pump and a condenser in a solvent recovery system to control an evaporation rate of a solvent in the reactor by adjusting a vacuum degree; then maintaining a reaction temperature in the reactor at 25-30° C. and reacting for 2.5h; wherein at this time, the material in the reactor is a sludge form.

Injecting 50-80° C. hot water into a jacket of the reactor, and drying for 1h under a vacuum degree of −0.04-−0.05 MPa, so as to obtain powdered sodium isobutyl xanthate as well as recover the solvent.

Opening a discharge valve of the reactor to transfer the powdered sodium xanthate obtained by the reaction into a twin-screw extruder for granulation, so as to obtain granular sodium xanthate with a size of about Φ4×6-12 (mm).

Sending the granular sodium xanthate into a disc dryer for further drying to remove residual solvent and a part of water at a drying temperature of 50-120° C., so as to obtain a dried granular sodium isobutyl xanthate product as well as recover the solvent.

Analysis showed that the sodium isobutyl xanthate product had a purity of 90.39%, a free base content of 0.08%, and a moisture content of 3.48%. A yield of the product based on isobutanol was 96.13%, and the product reached a standard dry product of nonferrous metal industry.

Embodiment 4: Preparing Sodium Isobutyl Xanthate with the System of the Embodiment 1

Adding 27.2 parts of 99% pure dichloromethane and 24.4 parts of 99% pure carbon disulfide to a slurry reactor, turning on a reactor stirring device, and then adding 6.4 parts of granular sodium hydroxide (99% pure) to the reactor; then dropping 11.8 parts of 99% pure isobutanol into the reactor; when material temperature in the reactor rises rapidly with reaction, turning on a vacuum pump and a condenser in a solvent recovery system to control an evaporation rate of a solvent in the reactor by adjusting a vacuum degree; then maintaining a reaction temperature in the reactor at 25-30° C., and reacting for 2.5h; wherein at this time, the material in the reactor is a sludge form.

Injecting 70-80° C. hot water into a jacket of the reactor, and drying for 2h under a vacuum degree of −0.04-−0.05 MPa, so as to obtain powdered sodium isobutyl xanthate as well as recover the solvent.

Analysis showed that the sodium isobutyl xanthate product had a purity of 87.4% and a free base content of 0.20%. A yield of the product based on isobutanol was 97.35%, and the product reached a standard special grade product of nonferrous metal industry.

Embodiment 5: Preparing Sodium Ethyl Xanthate with the System of the Embodiment 1

Adding 48.2 parts of 99% pure dichloromethane and 16.2 parts of 99% pure carbon disulfide to a slurry reactor, turning on a reactor stirring device, and then adding 5.7 parts of granular sodium hydroxide (99% pure) to the reactor; then dropping 6.5 parts of 99% pure absolute ethanol into the reactor; when material temperature in the reactor rises rapidly with reaction, turning on a vacuum pump and a condenser in a solvent recovery system to control an evaporation rate of a solvent in the reactor by adjusting a vacuum degree; then maintaining a reaction temperature in the reactor at 25-30° C., and reacting for 2.5h; wherein at this time, the material in the reactor is a sludge form.

Injecting 70-90° C. hot water into a jacket of the reactor, and drying for 1h under a vacuum degree of −0.03-−0.05 MPa, so as to obtain powdered sodium ethyl xanthate as well as recover the solvent.

Opening a discharge valve of the reactor to transfer the powdered sodium xanthate obtained by the reaction into a twin-screw extruder for granulation, so as to obtain granular sodium ethyl xanthate with a size of about Φ4×6-12 (mm).

Sending the granular sodium ethyl xanthate into a disc dryer for further drying to remove residual solvent and a part of water at a drying temperature of 50-120° C., so as to obtain a dried granular sodium ethyl xanthate product as well as recover the solvent.

Analysis showed that the sodium ethyl xanthate product had a purity of 92.03%, a free base content of 0.11%, and a moisture content of 2.13%. A yield of the product based on ethanol was 94.89%, and the product reached a standard dry product of nonferrous metal industry.

Embodiment 6: Preparing Sodium n-Butyl Xanthate with the System of the Embodiment 1

Adding 41.6 parts of 99% pure dichloromethane and 16.0 parts of 99% pure carbon disulfide to a slurry reactor, turning on a reactor stirring device, and then adding 5.6 parts of granular sodium hydroxide (99% pure) to the reactor, wherein a material temperature in the reactor is 28° C.; then dropping 10.4 parts of 99% pure n-butanol into the reactor; when material temperature in the reactor rises rapidly with reaction, turning on a vacuum pump and a condenser in a solvent recovery system to control an evaporation rate of a solvent in the reactor by adjusting a vacuum degree; then maintaining a reaction temperature in the reactor at 25-30° C., and reacting for 2.5h; wherein at this time, the material in the reactor is a sludge form.

Injecting 50-80° C. hot water into a jacket of the reactor, and drying for 2.5h under a vacuum degree of −0.05-−0.06 MPa, so as to obtain powdered sodium n-butyl xanthate as well as recover the solvent.

Analysis showed that the sodium n-butyl xanthate product had a purity of 84.7% and a free base content of 0.09%. A yield of the product based on n-butanol was 95.73%, and the product reached a standard first grade product of nonferrous metal industry.

Embodiment 7: Preparing Mixed Sodium Xanthate with the Device of the Embodiment 1

Adding 34.0 parts of 99% pure dichloromethane and 18.3 parts of 99% pure carbon disulfide to a slurry reactor, turning on a reactor stirring device, and then adding 6.4 parts of granular sodium hydroxide (99% pure) to the reactor; then dropping 11.4 parts of 99% pure isobutanol and 0.7 parts of 99% pure 2-tert-butoxyethanol into the reactor; when material temperature in the reactor rises rapidly with reaction, turning on a vacuum pump and a condenser in a solvent recovery system to control an evaporation rate of a solvent in the reactor by adjusting a vacuum degree; then maintaining a reaction temperature in the reactor at 25-30° C., and reacting for 2.5h; wherein at this time, the material in the reactor is a sludge form.

Injecting 50-80° C. hot water into a jacket of the reactor, and drying for 1h under a vacuum degree of −0.04--−0.05 MPa, so as to obtain powdered mixed sodium xanthate as well as recover the solvent.

Opening a discharge valve of the reactor to transfer the powdered sodium xanthate obtained by the reaction into a twin-screw extruder for granulation, so as to obtain granular mixed sodium xanthate with a size of about Φ4×6-12 (mm).

Sending the granular mixed sodium xanthate into a disc dryer for further drying to remove residual solvent and a part of water at a drying temperature of 50-120° C., so as to obtain a dried granular mixed sodium xanthate product as well as recover the solvent.

Analysis showed that the mixed sodium xanthate product had an average content of 90.23%, a free base content of 0.18%, and a moisture content of 3.41%. A yield of the product based on sodium hydroxide was 93.09%.

Embodiment 8: Preparing Mixed Sodium Xanthate with the Device of the Embodiment 1

Adding 34.0 parts of 99% pure dichloromethane and 18.3 parts of 99% pure carbon disulfide to a slurry reactor, turning on a reactor stirring device, and then adding 6.4 parts of granular sodium hydroxide (99% pure) to the reactor; then dropping 9.1 parts of mixed alcohol (containing 50% isobutanol and 50% absolute ethanol) into the reactor; when material temperature in the reactor rises rapidly with reaction, turning on a vacuum pump and a condenser in a solvent recovery system to control an evaporation rate of a solvent in the reactor by adjusting a vacuum degree; then maintaining a reaction temperature in the reactor at 25-30° C., and reacting for 2.5h; wherein at this time, the material in the reactor is a sludge form.

Injecting 50-80° C. hot water into a jacket of the reactor, and drying for 1h under a vacuum degree of −0.04--−0.05 MPa, so as to obtain powdered mixed sodium xanthate as well as recover the solvent.

Opening a discharge valve of the reactor to transfer the powdered sodium xanthate obtained by the reaction into a twin-screw extruder for granulation, so as to obtain granular mixed sodium xanthate with a size of about Φ4×6-12 (mm).

Sending the granular mixed sodium xanthate into a disc dryer for further drying to remove residual solvent and a part of water at a drying temperature of 50-120° C., so as to obtain a dried granular mixed sodium xanthate product as well as recover the solvent. Analysis showed that the product had an average content of 90.77%, a free base content of 0.16%, and a moisture content of 3.78%. A yield of the product based on sodium hydroxide was 92.79%.

Comparison 1: Preparing Sodium Isobutyl Xanthate by a Kneading Method

Adding 275.8 parts of 99% pure carbon disulfide and 255.7 parts of 99% pure isobutanol to the kneader; kneading, and injecting freezing brine to maintain a mixture temperature below 20° C.; then slowly adding 138.4 parts of powdered sodium hydroxide (99% pure) while controlling a reaction temperature below 35° C.; then, kneading at 20-35° C. for 4h to complete reaction, so as to obtain a powdered sodium isobutyl xanthate product. Analysis showed that the sodium isobutyl xanthate product had a purity of 84.12% and a free base content of 0.46%. A yield of the product based on isobutanol was 91.74%, and the product reached a standard first grade product of nonferrous metal industry.

Comparison 2: Preparing Sodium Ethyl Xanthate by a Kneading Method

Adding 343.8 parts of 99% pure carbon disulfide and 198.1 parts of 99% pure absolute ethanol to the kneader; kneading, and injecting freezing brine to maintain a mixture temperature below 20° C.; then slowly adding 172.0 parts of powdered sodium hydroxide (99% pure) while controlling a reaction temperature below 30° C.; then, kneading at 20-35° C. for 4h to complete reaction, so as to obtain a powdered sodium ethyl xanthate product. Analysis showed that the sodium ethyl xanthate product had a purity of 82.44% and a free base content of 0.41%. A yield of the product based on ethanol was 90.65%, and the product reached a standard first grade product of nonferrous metal industry.

From the results of the two comparisons, it can be seen that the sodium xanthate prepared in the embodiments of the present invention has high purity, low free alkali content, low moisture content, and high product yield.

The above are only preferred embodiments of the present invention and are not intended to be limiting. Any modification, equivalent replacement, improvement and the like made within the spirit and principles of the present invention should fall within the scope of protection of the present invention.

What is claimed is:

1. A method for preparing powdered xanthate by a slurry method, comprising steps of:
   1) adding dichloromethane and carbon disulfide into a slurry reactor and mixing through stirring, then adding an alcohol and an alkali and stirring for reaction; wherein the alcohol is $C_2$-$C_{12}$ fatty alcohol selected from the group consisting of ethanol, n-propanol, isopropanol, n-butanol, isobutanol, amyl alcohol, isoamyl alcohol, neopentyl alcohol, n-hexanol, isohexanol, methyl isobutyl carbinol, n-octanol, isooctyl alcohol, and dodecanol; the alkali is selected from sodium hydroxide and potassium hydroxide, in shape of powder, granule or flake;
   2) turning on a vacuum pump to adjust a system pressure when a temperature of a reaction system begins to rise, so as to control the temperature of the reaction system and recover a solvent; and
   3) injecting hot water or steam into a heating jacket of the slurry reactor after the solvent is recovered, so as to accelerate removal of the solvent and obtain powdered xanthate.

2. The method, as recited in claim 1, further comprising a step of: transferring the powdered xanthate to a granulation equipment for granulation; drying and dehydrating granules obtained by granulation to obtain granular xanthate.

3. The method, as recited in claim 1, wherein in the step 1), 2-tert-butoxyethanol is also added.

4. The method, as recited in claim 1, wherein a molar ratio of the alcohol, the alkali and the carbon disulfide is 1:1-1.05:1-3, and a volume of the dichloromethane is 0.5-5 times a volume of the alcohol.

5. The method, as recited in claim 1, wherein in the step 2), the system pressure is controlled at −0.01-0.081 MPa; and the temperature of the reaction system is maintained at 10-80° C.

6. The method, as recited in claim 1, wherein the reaction lasts for 0.5-6h.

* * * * *